United States Patent [19]
Kleemann et al.

[11] Patent Number: 5,856,344
[45] Date of Patent: Jan. 5, 1999

[54] SULFONYLAMINO-SUBSTITUTED BENZOYLGUANIDINES, A PROCESS FOR THEIR PREPARATION, THEIR USE AS A MEDICAMENT OR DIAGNOSTIC AID, AND MEDICAMENT CONTAINING THEM

[75] Inventors: Heinz-Werner Kleemann, Bischofsheim; Joachim Brendel, Bad Vilbel; Jan-Robert Schwark, Frankfurt; Andreas Weichert, Egelsbach; Hans Jochen Lang, Hofheim; Udo Albus, Florstadt; Wolfgang Scholz, Eschborn, all of Germany

[73] Assignee: Hoechst Aktiengesellschaft, Frankfurt, Germany

[21] Appl. No.: 741,588

[22] Filed: Oct. 31, 1996

[30]     Foreign Application Priority Data

Nov. 14, 1995 [DE]  Germany .................. 195 42 306.2

[51] Int. Cl.$^6$ .................. A61K 31/44; C07D 213/63; C07D 211/36; C07C 279/22
[52] U.S. Cl. .................. 514/346; 514/424; 514/634; 546/291; 548/543; 564/237
[58] Field of Search .................. 546/291, 296, 546/300; 548/543; 514/346, 424, 634; 564/237

[56]     References Cited

U.S. PATENT DOCUMENTS

| | | | |
|---|---|---|---|
| 3,780,027 | 12/1973 | Cargoe et al. | 549/494 |
| 5,091,394 | 2/1992 | Englert et al. | 514/331 |
| 5,140,039 | 8/1992 | DeBernardis et al. | 514/422 |
| 5,185,364 | 2/1993 | DeBernardis et al. | 514/444 |
| 5,292,755 | 3/1994 | Englert et al. | 514/331 |
| 5,364,868 | 11/1994 | Englert et al. | 514/331 |
| 5,373,024 | 12/1994 | Lang et al. | 514/618 |
| 5,395,826 | 3/1995 | Naumann et al. | 514/107 |
| 5,416,094 | 5/1995 | Lal et al. | 514/307 |
| 5,498,617 | 3/1996 | Naumann et al. | 514/315 |
| 5,516,805 | 5/1996 | Lang et al. | 514/620 |
| 5,547,953 | 8/1996 | Weichert et al. | 514/226.5 |
| 5,559,153 | 9/1996 | Schwark et al. | 514/597 |
| 5,567,734 | 10/1996 | Schwark et al. | 514/617 |
| 5,571,842 | 11/1996 | Kleemann et al. | 514/618 |
| 5,591,754 | 1/1997 | Lang et al. | 514/331 |

FOREIGN PATENT DOCUMENTS

| | | |
|---|---|---|
| 3301493 | 8/1993 | Australia . |
| 5271693 | 12/1993 | Australia . |
| 4163593 | 1/1994 | Australia . |
| 5527994 | 2/1994 | Australia . |
| 5236893 | 6/1994 | Australia . |
| 5249093 | 6/1994 | Australia . |
| 5522994 | 8/1994 | Australia . |
| 6454394 | 12/1994 | Australia . |
| 6454494 | 12/1994 | Australia . |
| 4221896 | 2/1995 | Australia . |
| 6881194 | 2/1995 | Australia . |
| 6884494 | 2/1995 | Australia . |
| 7150794 | 3/1995 | Australia . |
| 1635495 | 10/1995 | Australia . |
| 1786195 | 11/1995 | Australia . |
| 2330095 | 1/1996 | Australia . |
| 3050495 | 3/1996 | Australia . |
| 3050595 | 3/1996 | Australia . |
| 3050695 | 3/1996 | Australia . |
| 3900895 | 5/1996 | Australia . |
| 2168315 | 1/1996 | Canada . |
| 0325964 | 8/1989 | European Pat. Off. . |
| 9426709 | 11/1994 | WIPO . |
| 9604241 | 2/1997 | WIPO . |

OTHER PUBLICATIONS

Chemical Abstracts, vol. 125(7) abst. No. 86, 331–t, pub. Aug. 12, 1996.

Chemical Abstracts, vol. 125(9), abst. No. 114,323n, pub. Aug. 26, 1996.

Eur. Heart of J. 9(suppl. 1):25 and 167 (1988) book of abstracts.

Schmid, Andreas et al. *Biochemical and Biophysical Research Comm.* 112–117 (1992).

Scholz, Wolfgang et al. *Cardiovascular Res.* (1995) 29(2):260–8.

Rosskopf, Dieter et al. *Cellular Physiology Biochem* (1995), (5)4, 269–275.

Scholz, Wolfgang et al. *Basic Research Cardiology* (1993), 88(5), 443–55.

Sack, Stefan et al. *J. Cardiovasc. Pharmacol.* (1994)23(1), 72–78.

Kranzhofer, Roger et al. *Circ. Res.*,(1993), 73(2), 264–8.

Scholz, Wolfgang et al. *Br. J. Pharmacol.* (1993), 109(2), 562–8.

Scholz, Wolfgang et al. *J. Mol. Cell. Cardiol.* (1992), 24(7), 731–39.

(List continued on next page.)

*Primary Examiner*—Alan L. Rotman
*Attorney, Agent, or Firm*—Finnegan, Henderson, Farabow, Garrett & Dunner, L.L.P.

[57]     ABSTRACT

Benzoylguanidines of the formula I

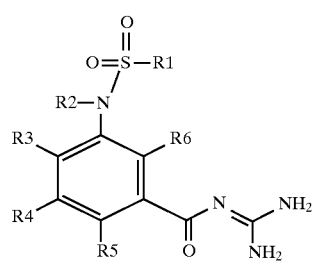

in which R(1) to R(6) have the meanings stated in the claims, are antiarrhythmic pharmaceuticals which have excellent activity and a cardioprotective component and are highly suitable for the prophylaxis of infarcts and the treatment of infarcts, and for the treatment of angina pectoris, in which case they also preventively inhibit or greatly reduce the pathophysiological processes in the development of ischemia-induced damage, especially in the triggering of ischemia-induced cardiac arrhythmias.

18 Claims, No Drawings

OTHER PUBLICATIONS

Scholz, Wolfgang et al. *Cardiovascular Research.* (Feb., 1995) vol. 29(2), 184–8.

*Biological Chemistry* Hoppe–Seyler (1991), vol. 372, No. 9, p. 750.

Mitsuka, Masayuki et al. *Circulation Research* (1993), vol. 73(2):269–275.

Duff, Henry J. et al., *Circulation*, 79(6), 1257–63 (1989).

Dixon, Robert P. et al., *J. Am Chem Soc.* (1992) 114 (1), 365–6.

SULFONYLAMINO-SUBSTITUTED BENZOYLGUANIDINES, A PROCESS FOR THEIR PREPARATION, THEIR USE AS A MEDICAMENT OR DIAGNOSTIC AID, AND MEDICAMENT CONTAINING THEM

BACKGROUND OF THE INVENTION

The invention relates to benzoylguanidines of the formula I

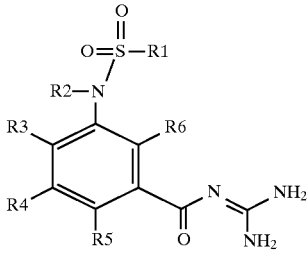

in which:
R(1) is alkyl having 1, 2, 3, 4, 5, 6, 7 or 8 carbon atoms or NR(7)R(8);
R(7) and R(8) are, independently of one another, hydrogen or alkyl having 1, 2, 3, 4, 5, 6, 7 or 8 carbon atoms
R(2) is hydrogen, alkyl having 1, 2, 3, 4, 5, 6, 7 or 8 carbon atoms or —$SO_2R(9)$ R(9) is independently defined as R(1);
R(3) is hydrogen, —SR(25), —OR(25), —NR(25)R(26) or —CR(25)R(26)R(27);
R(25) is hydrogen, alkyl having 1, 2, 3, 4, 5, 6, 7 or 8 carbon atoms or phenyl, which is unsubstituted or substituted by 1–3 substituents selected from the group consisting of F, Cl, $CF_3$, $CH_3$, methoxy, hydroxyl, amino, methylamino and dimethylamino;

or

R(25) is —($C_1$–$C_9$)-heteroaryl, which is unsubstituted or substituted by I - 3 substituents selected from the group consisting of the group F, Cl, $CF_3$, $CH_3$, methoxy, hydroxyl, amino, methylamino and dimethylamino;
R(26) and R(27) are, independently of one another, defined as R(25) or are hydrogen or alkyl having 1, 2, 3, 4, 5, 6, 7 or 8 carbon atoms;
R(4) is hydrogen, F, Cl, Br, I, OH, —C≡N, $CF_3$, alkyl having 1, 2, 3, 4, 5, 6, 7 or 8 carbon atoms, alkenyl having 2, 3, 4, 5, 6, 7 or 8 carbon atoms or —$(CH_2)_m$R(14);
m is zero, 1 or 2;
R(14) is —($C_3$–$C_8$)-cycloalkyl or phenyl, which is unsubstituted or substituted by 1–3 substituents selected from the group consisting of F and Cl, —$CF_3$, methyl, methoxy and —NR(15)R(16);
R(15) and R(16) are, independently of one another, hydrogen or —$CH_3$;
R(5) and R(6) are, independently of one another, hydrogen, alkyl having 1, 2, 3 or 4 carbon atoms, F, Cl, —OR(32), —NR(33)R(34) or $CF_3$;
R(32), R(33) and R(34) are, independently of one another, hydrogen or alkyl having 1, 2, 3 or 4 carbon atoms;
and their pharmaceutically acceptable salts.
Preferred compounds of the formula I are those in which:
R(1) is alkyl having 1, 2, 3 or 4 carbon atoms or NR(7)R(8);
R(7) and R(8) are, independently of one another, hydrogen or alkyl having 1, 2, 3 or 4 carbon atoms;
R(2) is hydrogen, alkyl having 1, 2, 3 or 4 carbon atoms or —$SO_2R(9)$ R(9) is independently defined as R(1);
R(3) is hydrogen, —SR(25), —OR(25), —NR(25)R(26) or —CR(25)R(26)R(27);
R(25) is hydrogen, alkyl having 1, 2, 3 or 4 carbon atoms or phenyl, which is unsubstituted or substituted by 1–2 substituents selected from the group consisting of F, Cl, $CF_3$, $CH_3$, methoxy and dimethylamino;

or

R(25) is —($C_1$–$C_9$)-heteroaryl, which is unsubstituted or substituted by 1–2 substituents selected from the group consisting of F, Cl, $CF_3$, $CH_3$, methoxy and dimethylamino;
R(26) and R(27) are, independently of one another, hydrogen or alkyl having 1, 2, 3 or 4 carbon atoms;
R(4) is hydrogen, F, Cl, Br, I, OH, $CF_3$, alkyl having 1, 2, 3 or 4 carbon atoms, alkenyl having 2, 3 or 4 carbon atoms or —$(CH_2)_m$R(14);
m is zero, 1 or 2;
R(14) is —($C_3$–$C_6$)-cycloalkyl or phenyl, which is unsubstituted or substituted by 1–2 substituents selected from the group consisting of F, Cl, —$CF_3$, methyl and methoxy;
R(5) and R(6) are, independently of one another, hydrogen, alkyl having 1, 2 or 3 carbon atoms, F, Cl, —OR(32), —NR(33)R(34) or $CF_3$;
R(32), R(33) and R(34) are, independently of one another, hydrogen or methyl;
and their pharmaceutically acceptable salts.
Particularly preferred compounds of the formula I are those in which:
R(1) is methyl or dimethylamino;
R(2) is hydrogen, methyl, —$SO_2CH_3$ or —$SO_2N(CH_3)_2$;
R(3) is hydrogen, —SR(25), —OR(25), —NR(25)R(26) or —CR(25)R(26)R(27);
R(25) is hydrogen, alkyl having 1, 2 or 3 carbon atoms or phenyl, which is unsubstituted or substituted by one substituent selected from the group consisting of F, Cl, $CF_3$ and $CH_3$;

or

R(25) is —($C_1$–$C_9$)-heteroaryl, which is unsubstituted or substituted by one substituent selected from the group consisting of F, Cl, $CF_3$ and $CH_3$;
R(26) and R(27) are, independently of one another, hydrogen or methyl;
R(4) is hydrogen, F, Cl, OH, $CF_3$ or alkyl having 1, 2, 3 or 4 carbon atoms;
R(5) and R(6) are, independently of one another, hydrogen, alkyl having 1, 2 or 3 carbon atoms, F, Cl, —OR(32), —NR(33)R(34) or $CF_3$;
R(32), R(33) and R(34) are, independently of one another, hydrogen or methyl;
and their pharmaceutically acceptable salts.
Very particularly preferred compounds of the formula I are those in which:
R(1) is methyl or dimethylamino;
R(2) is hydrogen;
R(3) is hydrogen, —OR(25) or —CR(25)R(26)R(27);
R(25) is hydrogen, alkyl having 1, 2 or 3 carbon atoms or phenyl, which is unsubstituted or substituted by one substituent selected from the group consisting of F, Cl, $CF_3$ and $CH_3$;

or

R(25) is —(C$_1$–C$_9$)-heteroaryl, which is unsubstituted or substituted by one substituent selected from the group consisting of F, Cl, CF$_3$ and CH$_3$;

R(26) and R(27) are, independently of one another, hydrogen or methyl;

R(4) is hydrogen, OH, CF$_3$ or alkyl having 1, 2, 3 or 4 carbon atoms;

R(5) and R(6) are, independently of one another, hydrogen, alkyl having 1, 2 or 3 carbon atoms, F, Cl or CF$_3$;

and their pharmaceutically acceptable salts.

The specified alkyl radicals can be present both straight-chain and branched.

(C$_1$–C$_9$)-Heteroaryl means radicals which are derived from phenyl or naphthyl in which one or more CH groups are replaced by N and/or in which at least two adjacent CH groups are replaced by S, NH or O (to form a five-membered aromatic ring). It is furthermore possible for one or both carbon atoms at the point of fusion of bicyclic radicals to the nitrogen atoms (as in indolizinyl).

Particularly appropriate as heteroaryl is furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl, Heterocycles which are very particularly suitable are thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, indolyl, quinolyl and isoquinolyl.

If one of the substituents R(1) to R(6) contains one or more centers of asymmetry, these can have, independently of one another, both the S and R configuration. The compounds can be in the form of optical isomers, of diastereomers, of racemates or as mixtures thereof.

The invention furthermore relates to a process for the preparation of the compounds I, which comprises reacting compounds of the formula II

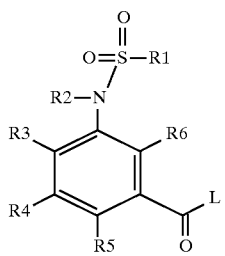

II in which R(1) to R(6) have the abovementioned meanings, and L is a leaving group readily amenable to nucleophilic substitution, with guanidine. The activated acid derivatives of the formula II in which L is an alkoxy, preferably a methoxy group or phenoxy group, a phenylthio, methylthio, 2-pyridylthio group, or a nitrogen heterocycle, preferably 1-imidazolyl, are advantageously obtained in a manner known per se from the underlying carbonyl chlorides (formula II, L=Cl), which in turn can be prepared in a manner known per se from the underlying carboxylic acids (formula II, L=OH), for example with thionyl chloride. Besides the carbonyl chlorides of the formula II (L=Cl), other activated acid derivatives of the formula II can also be prepared in a manner known per se directly from the underlying benzoic acid derivatives (formula II, L=OH), such as, for example, the methyl esters of the formula II with L=OCH$_3$ by treating with gaseous HCl in methanol, the imidazolides of the formula II by treatment with carbonyl-diimidazole [L=1-imidazolyl, Staab, Angew. Chem. Int. Ed. Engl. 1,351–367 (1962)], the mixed anhydrides II with Cl—COOC$_2$H$_5$ or tosyl chloride in the presence of triethylamine in an inert solvent, as well as the activations of benzoic acids with dicyclohexylcarbodiimide (DCC) or with O-[(cyano(ethoxycarbonyl)methylene)amino]-1,1,3,3-tetramethyluronium tetrafluoroborate ("TOTU") [Proceedings of the 21. European Peptide Symposium, Peptides 1990, Editors E. Giralt and D. Andreu, Escom, Leiden, 1991]. A number of suitable methods for preparing activated carboxylic acid derivatives of the formula II is indicated in J. March, Advanced Organic Chemistry, Third Edition (John Wiley & Sons, 1985), page 350, indicated source literature.

The reaction of an activated carboxylic acid derivative of the formula I with guanidine takes place in a manner known per se in a protic or aprotic polar but inert organic solvent. In this connection, for the reaction of the methyl benzoates (II, L=OMe) with guanidine, methanol, isopropanol or THF have proven suitable at between 20° C. and the boiling point of these solvents. Most reactions of compounds II with salt-free guanidine have advantageously been carried out in inert solvents such as THF, dimethoxyethane, dioxane or isopropanol. However, water can also be used as the solvent.

When L=Cl, it is advantageous to add an acid trap, for example in the form of excess guanidine to bind the hydrohalic acid.

The introduction of the benzenesulfonamide derivatives which are substituted in the phenyl moiety by sulfur, oxygen or nitrogen nucleophiles takes place by methods known from the literature for nucleophilic substitution on derivatives of 3-nitrobenzoic acid. Halides and trifluoromethane-sulfonates have proven suitable as leaving group on the benzoic acid derivative in this substitution. It is advantageous to use a dipolar aprotic solvent such as DMF or TMU, at a temperature from 0° C. to the boiling point of the solvent, preferably from 80° C. to the boiling point of the solvent. Advantageously used as acid trap is an alkali metal or alkaline earth metal salt with an anion of high basicity and low nucleophilicity, for example K$_2$CO$_3$ or Cs$_2$CO$_3$.

The reduction of the nitro compound to the aniline can make use of the standard processes which have been known for some time. Suitable examples are reduction with iron powder in methanol and concentrated aqueous HCl solution.

Surprisingly, the nitro group can also be converted directly into the methanesulfonylamino group using sodium methanesulfinate. To do this, the nitro compound is reacted with sodium methanesulfinate in a dipolar aprotic solvent such as, for example, DMF, TMU or NMP, at a temperature between RT and the boiling point of the solvent, preferably from 80° C. to 160° C.

The introduction of the alkyl or aryl substituents takes place by methods known from the literature of palladium-mediated cross-coupling of aryl halides with, for example, organozinc compounds, organostannanes, organoboronic acids or organoboranes.

Benzoylguanidines I are generally weak bases and are able to bond acid to form salts. Suitable acid addition salts are salts of all pharmacologically suitable acids, for example halides, in particular hydrochlorides, ascorbates, lactates, sulfates, citrates, tartrates, acetates, phosphates, methylsulfonates, p-toluenesulfonates.

Benzoylguanidines are described in U.S. Pat. No. 5 091 394 (HOE 89/F 288) and European Published Specification 0 556 674 (HOE 92/F 034), but in these the substituents do not have the meanings claimed in the present invention. No phenylsulfamide derivatives are described. In addition, the solubility in water of these known benzoylguanidines is unsatisfactory.

These also disclose benzoylguanidines with sulfamoyl substituents $R_2N-SO_2-$; however, no compounds of the type according to the invention which carry an aminosulfonyl group $-NR(2)SO_2-R(1)$ are disclosed.

The compounds are, as a subsequence of their pharmacological properties, outstandingly suitable as antiarrhythmic pharmaceuticals with a cardioprotective component for the prophylaxis of infarcts and the treatment of infarcts, and for the treatment of angina pectoris, in which case they also preventively inhibit or greatly reduce the pathophysiological processes in the development of ischemia-induced damage, especially in the triggering of ischemia-induced cardiac arrhythmias. Because of their protective effect in pathological hypoxic and ischemic situations, the compounds of the formula I according to the invention can, as a consequence of inhibition of the cellular $Na^+/H^+$ exchange mechanism, be used as pharmaceuticals for the treatment of all acute or chronic damage induced by ischemia or disorders induced primarily or secondarily thereby. This relates to their use as pharmaceuticals for surgical interventions, for example in organ transplants, in which case the compounds can be used both to protect the organs in the donor before and during removal, protect removed organs, for example on treatment with or storage thereof in physiological bath liquids, and on transferring to the recipient organism. The compounds are likewise valuable pharmaceuticals which have a protective effect when performing angioplastic surgical interventions, for example on the heart and on peripheral vessels. In accordance with their protective effect on ischemia-induced damage, the compounds are also suitable as pharmaceuticals for the treatment of ischemias of the nervous system, especially the CNS, in which case they are suitable, for example, for treating stroke or cerebral edema. In addition, the compounds of the formula I according to the invention are likewise suitable for treatments of types of shock such as, for example, of allergic, cardiogenic, hypovolemic and bacterial shock.

Furthermore, the compounds of the formula I according to the invention are distinguished by a potent inhibitory effect on the proliferation of cells, for example of fibroblast cell proliferation and the proliferation of smooth vascular muscle cells. The compounds of the formula I are therefore suitable as valuable therapeutic agents for diseases in which cell proliferation represents a primary or secondary cause, and can therefore be used as antiatherosclerotics, agents for late complications of diabetes, cancers, fibrotic disorders such as pulmonary fibrosis, liver fibrosis or kidney fibrosis, organ hypertrophies and hyperplasias, especially in prostate hyperplasia and prostate hypertrophy.

The compounds according to the invention are effective inhibitors of the cellular sodium/proton antiporter ($Na^+/H^+$ exchanger), which is elevated in numerous disorders (essential hypertension, atherosclerosis, diabetes etc.) also in those cells which are readily accessible to measurements, such as, for example, in erythrocytes, platelets or leukozytes. The compounds according to the invention are therefore suitable as outstanding and simple scientific tools, for example in their use as diagnostic aids for determining and distinguishing certain types of hypertension, but also of atherosclerosis, of diabetes, of proliferative disorders etc. Furthermore, the compounds of the formula I are suitable for preventive therapy to prevent the development of high blood pressure, for example of essential hypertension.

Compared with most of the known compounds, the compounds according to the invention display a significantly improved solubility in water. They are therefore considerably more suitable for i.v. administration.

The compounds according to the invention are distinguished from the known compounds with good solubility in water by their better bioavailabiity and pharmacokinetics.

Pharmaceuticals which contain a compound I can moreover be administered orally, parenterally, intravenously, rectally or by inhalation, with the preferred administration depending on the particular manifestation of the disorder. The compounds I can moreover be used alone or together with pharmaceutical ancillary substances, specifically in veterinary and in human medicine.

The particular ancillary substances suitable for the required pharmaceutical formulation are familiar to the skilled worker on the basis of his expert knowledge. Besides solvents, gel formers, suppository bases, tablet auxiliaries and other active substance vehicles, it is preferable to use for example, antioxidants, dispersants, emulsifiers, antifoams, flavors, preservatives, solubilizers or colorants.

For a form for oral use, the active compounds are mixed with additives suitable for this purpose, such as excipients, stabilizers or inert diluents, and converted by conventional methods into suitable dosage forms such as tablets, coated tablets, hard gelatin capsules, aqueous, alcoholic or oily solutions. Examples of inert vehicles which can be used are gum arabic, magnesia, magnesium carbonate, potassium phosphate, lactose, glucose or starch, especially corn starch. This preparation can take place either as dry or as wet granules. Examples of suitable oily excipients or solvents are vegetable oils or animal oils, such as sunflower oil or fishliver oil.

For subcutaneous or intravenous administration, the active compounds are converted, if required with the substances customary for this purpose, such as solubilizers, emulsifiers or other ancillary substances, into a solution, suspension or emulsion. Examples of suitable solvents are: water, physiological saline or alcohols, for example ethanol, propanol, glycerol, as well as sugar solutions such as glucose or mannitol solutions or else a mixture of the various solvents mentioned.

Examples of suitable pharmaceutical formulations for administration in the form of aerosols or sprays are solutions, suspensions or emulsions of the active substance of the formula I in a pharmaceutically acceptable solvent such as, in particular, ethanol or water, or a mixture of such solvents. The formulation can also, if required, contain other pharmaceutical ancillary substances such as surfactants, emulsifiers and stabilizers, and a propellant gas. A formulation of this type normally contains the active substance in a concentration of about 0.1 to 10, in particular of about 0.3 to 3% by weight.

The dosage of the active substance of the formula I to be administered, and the frequency of administration, depend on the potency and duration of action of the compounds used; also on the nature and severity of the disease to be treated and on the sex, age, weight and individual response of the mammal to be treated.

On average, the daily dose of a compound of the formula I for a patient weighing about 75 kg is at least 0.001 mg/kg of body weight, preferably at least 0.01 mg/kg of body weight, to a maximum of 10 mg/kg of body weight, preferably up to a maximum of 1 mg/kg of body weight. It is also possible in the case of acute episodes of the is disease, for example immediately after suffering a myocardial infarct, for even higher and, in particular, more frequent doses to be necessary, for example up to 4 single doses per day. Up to 100 mg per day may be necessary, especially on i.v. use, for example for an infarct patient in intensive care.

List of abbreviations:
AIBN α,α-azobisisobutyronitrile
Bn benzyl
Brine saturated aqueous NaCl solution
$CH_2Cl_2$ dichloromethane
DCI desorption chemical ionization
DIP diisopropyl ether
DMA dimethylacetamide
DME dimethoxyethane
DMF N,N-dimethylformamide
EA ethyl acetate (EtOAc)
EI electron impact
eq equivalent
ES elektrospray ionization
Et ethyl
FAB fast atom bombardment
HEP n-heptane
HOAc acetic acid
Me methyl
MeOH methanol
mp melting point
MTB methyl tertiary-butyl ether
NBS N-bromosuccinimide
NMP N-methylpyrrolidone
RT room temperature
THF tetrahydrofuran
TMU N,N,N',N'-tetramethylurea
Tol toluene
CNS central nervous system Experimental part General method for the preparation of benzoylguanidines (I)

Variant A: from benzoic acids (II, L=OH)

0.01M of the benzoic acid derivative of the formula II is dissolved or suspended in 60 ml of anhydrous THF and then 1.78 g (0.011 mol) of carbonyldiimidazole are added. After stirring at RT for 2 hours, 2.95 g (0.05 mol) of guanidine are introduced into the reaction solution. After stirring overnight, the THF is removed by distillation under reduced pressure (rotary evaporator), water is added, the pH is adjusted to 6 to 7 with 2N HCl, and the appropriate benzoylguanidine (formula I) is filtered off. The benzoylguanidines obtained in this way can be converted into corresponding salts by treatment with aqueous, methanolic or ethereal hydrochloric acid or other pharmacologically suitable acids.

General method for the preparation of benzoylguanidines (I)

Variant B: from alkyl benzoates (II, L=O-alkyl)

5 mmol of the alkyl benzoate of the formula II and 25 mmol of guanidine (free base) are dissolved in 15 ml of isopropanol or suspended in 15 ml of THF and boiled under reflux until conversion is complete (thin-layer check) (typical reaction time 2 to 5 h). The solvent is removed by distillation under reduced pressure (rotary evaporator), the residue is taken up in 300 ml EA and washed 3 x with 50 ml of $NaHCO_3$ solution each time. It is dried over $Na_2SO_4$, the solvent is removed by distillation in vacuo, and chromatography is carried out on silica gel with a suitable mobile phase, for example EA/MeOH 5:1.
(Compare Variant A for salt formation)

General method for the preparation of benzoylguanidines (I)

Variant C: From alkyl benzoates (II, L=O-alkyl), guanidine liberation in situ 25 mmol of potassium t-butoxide are dissolved in 100 ml of DMF (anhydrous), and 30 mmol of guanidine hydrochloride are added. The mixture is stirred at RT for 1 h and then 5 mmol of the alkyl benzoate of the formula II are added, and the mixture is stirred at RT (typical reaction time 1–24 h) or at 80° C. (typical reaction time 10 minutes to 4 h) until conversion is complete (thin-layer check). The reaction mixture is poured into 500 ml of water, adjusted to pH=8–9 with dilute aqueous HCl solution, stirred for 1 h and filtered with suction. The product is dried in vacuo and, if necessary, chromatographed on silica gel with a suitable mobile phase, for example EA/MeOH 5:1. (Compare Variant A for salt formation)

EXAMPLE 1

4-Isopropyl-3-methylsulfonylaminobenzoylguanidine, hydrochloride

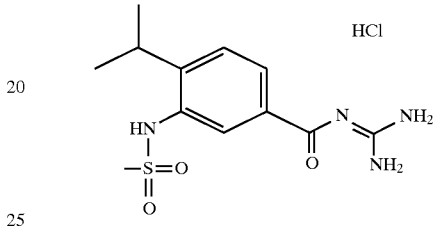

a) Methyl 4-isopropyl-3-methylsulfonylaminobenzoate 1.46 g of methyl 4-isopropyl-3-nitrobenzoate and 1.34 g of sodium methanesulfinate are heated under reflux in DMF for 4 h. After cooling to RT, the reaction mixture is added to 100 ml of saturated aqueous $NaHCO_3$ solution and extracted 3 times with 100 ml of EA each time. After drying over $Na_2SO_4$, the solvent is removed in vacuo. Chromatography of the residue on silica gel with DIP affords 400 mg of a colorless oil.

$R_f$ (DIP)=0.14 MS (DCI):272 $(M+H)^+$ b) 4-Isopropyl-3-methylsulfonylaminobenzoylguanidine 380 mg of methyl 4-isopropyl-3-methylsulfonylaminobenzoate are reacted with 414 mg of guanidine in 10 ml of i-propanol by the general method for the preparation of benzoylguanidines, Variant B. Chromatography on silica gel with EA/MeOH 5:1 results in 110 mg of an amorphous solid which is converted with aqueous HCl solution into the hydrochloride. mp (hydrochloride) 224° C.

$R_f$ (EA/MeOH 5:1)=0.39 MS (ES):299 $(M+H)^+$

EXAMPLE 2

3-Methylsulfonylamino-4—(3-pyridyloxy)benzoylguanidine

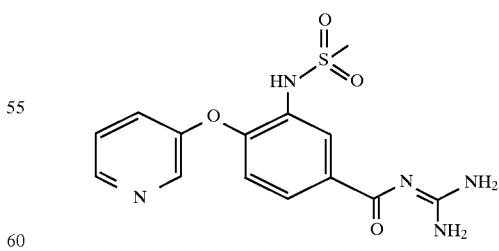

a) Methyl 3-nitro-4—(3-pyridyloxy)benzoate 30 g of 3-hydroxypyridine, 68 g of methyl 4-chloro-3-nitrobenzoate and 87 g of $K_2CO_3$ are stirred in 500 ml of NMP at 120° C. for 1 h. After cooling to RT, the mixture is poured into 3 l of water and extracted 3 times with 1 l of $CH_2Cl_2$ each time. The organic phase is subsequently washed twice with 1 l of water each time and dried over $Na_2SO_4$, and the solvent is removed in vacuo. 71 g of a brown oil which partially crystallizes and can be used without further purification are obtained.

$R_f$ (EA)=0.39 MS (EI):274 (M)$^+$ b) Methyl 3-amino-4-(3-pyridyloxy)benzoate 71 g of methyl 3-nitro-4-(3-pyridyloxy)benzoate and 52 g of iron powder are stirred in 500 ml of MeOH and, at RT, 500 ml of saturated aqueous HCl solution are slowly added. The mixture is then stirred at RT for 2 h and then the volatile constituents are removed in vacuo. The residue is stirred with 300 ml of saturated aqueous $Na_2CO_3$ solution (pH=11), and the precipitate is filtered off with suction. This precipitate is then extracted by boiling twice with 500 ml of EA each time, and the filtrate is extracted twice with 500 ml of EA each time. The combined EA phase is washed twice with 500 ml of water each time and dried over $Na_2SO_4$, and the solvent is removed in vacuo. 30 g of yellow-brown crystals, mp 101° C., are obtained.

$R_f$ (MTB)=0.32 MS (EI): 244 (M)$^+$ c) Methyl 3-bis(methylsulfonyl)amino-4-(3-pyridyloxy) benzoate 1 g of methyl 3-amino-4-(3-pyridyloxy) benzoate and 1 ml of triethylamine are dissolved in 30 ml of $CH_2Cl_2$, and 400 μl of methansulfonyl chloride are slowly added dropwise. The mixture is stirred at RT overnight, then diluted with 100 ml of $CH_2Cl_2$ and washed once with 100 ml of saturated aqueous $Na_2CO_3$ solution. After drying over $Na_2SO_4$, the solvent is removed in vacuo. 1.5 g of a pale yellow oil are obtained.

$R_f$ (MTB)=0.28 MS (EI):400 (M)$^+$ d) i-Propyl 3-methylsulfonylamino-4-(3-pyridyloxy) benzoate 1.5 g of methyl 3-bis(methylsulfonyl)amino-4-(3-pyridyloxy)benzoate and 1.1 g of guanidine are dissolved in 10 ml of i-propanol and heated under reflux for 2 h. The solvent is removed in vacuo, 200 ml of water are added, the pH is adjusted to 7 with aqueous HCl solution, and the mixture is extracted 3 times with 100 ml of EA each time. After drying over $Na_2SO_4$, the solvent is removed in vacuo. Chromatography on silica gel with EA/MeOH 5:1 affords 570 mg of a colorless oil.

$R_f$ (EA/MeOH 5:1)=0.46 MS (ES):351 (M+H)$^+$ e) 3-Methylsulfonylamino-4-(3-pyridyloxy)-benzoylguanidine 570 mg of i-propyl 3-methylsulfonylamino-4-(3-pyridyloxy)benzoate and 600 mg of guanidine are reacted in 2 ml of i-propanol by the general method for the preparation of benzoylguanidines, Variant B (reaction time 3 h). Chromatography on silica gel with EA/MeOH 5:1 results in 160 mg of an amorphous solid. A sample is converted with aqueous HCl solution into the hydrochloride which, because of its exceptionally hygroscopic properties, likewise does not provide a defined melting point.

$R_f$ (EE/MeOH 5:1)=0.13 MS (ES):350 (M+H)$^+$

EXAMPLE 3

2-Methyl-4-isopropyl-5-methylsulfonylaminobenzoylguanidine

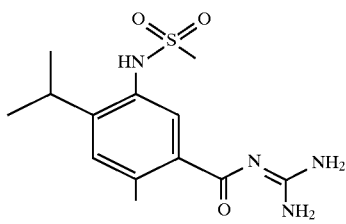

a) 2-Methyl-4-brom-5-nitrobenzoic acid 200 ml of $H_2SO_4$ are slowly added dropwise to 200 ml of a 65% aqueous $HNO_3$ solution. Then, at 0° C., 30 g of 4-bromo-2-methylbenzoic acid are added, and the mixture is stirred at this temperature for 3 h. The reaction mixture is poured onto 800 g of ice and then stirred for 1 h, and the product is filtered off and dried. 33 g of a colorless solid are obtained, mp 164° C. (contains a small amount of 3-nitro isomer).

MS (DCI):260 (M+H)$^+$ b) Methyl 2-methyl-4-brom-5-nitrobenzoate 33 g of 2-methyl-4-brom-5-nitrobenzoic acid are dissolved in 500 ml of MeOH, and 26.7 ml of $SOCl_2$ are slowly added. The mixture is boiled under reflux for 3 h and then the volatile constituents are removed in vacuo. The residue is mixed with 100 ml of toluene, and the volatile constituents are again removed in vacuo. 37 g of colorless crystals are obtained and are recrystallized from DIP to remove the 3-nitro isomers. 17 g of product are obtained from this, mp 104° C.

$R_f$ (EA/HEP 1:4)=0.26 MS (DCI):274 (M+H)$^+$ c) Methyl 2-methyl-4-brom-5-aminobenzoate 13 g of methyl 2-methyl-4-brom-5-nitrobenzoate are dissolved in 200 ml of MeOH, and 11.5 g of iron powder are added. Subsequently 200 ml of a saturated aqueous HCl solution are slowly added dropwise. The mixture is stirred at RT for 2 h, the volatile constituents are removed in vacuo, the residue is taken up in 400 ml of $Na_2CO_3$ and 200 ml of EA, and the mixture is filtered. The residue is boiled 3 times with 600 ml of EA for 15 minutes each time, and the aqueous phase is extracted twice with 200 ml of EA each time. The EA phases are combined and dried over $Na_2SO_4$, and the solvent is removed in vacuo. 7.6 g of a dark oil are obtained.

$R_f$ (EA/HEP 1:4)=0.14 MS (DCI):244 (M+H)$^+$ d) Methyl 2-methyl-4-brom-5-(di-methylsulfonyl) aminobenzoate 7.6 g of methyl 2-methyl-4-brom-5-aminobenzoate are dissolved in 300 ml of $CH_2Cl_2$, 21.5 ml of triethylamine are added and, at 0° C., 5.1 ml of methanesulfonyl chloride are added dropwise, and the mixture is stirred at RT for 2 h. The reaction mixture is stirred into 300 ml of a saturated aqueous $NaHCO_3$ solution, the $CH_2Cl_2$ phase is separated off, and 3 further extractions are carried out with 200 ml of EA each time. The combined organic phases are dried over $Na_2SO_4$, and the solvents are removed in vacuo. 10.9 g of yellow crystals are obtained, mp 221° C.

$R_f$ (DIP)=0.42 MS (DCI):399 (M)$^+$ e) Methyl 2-methyl-4-brom-5-methylsulfonylaminobenzoate 2.9 g of methyl 2-methyl-4-brom-5-(dimethylsulfonyl)aminobenzoate and 0.81 g of potassium t-butoxide are stirred in 100 ml of MeOH at RT for 4 h. The reaction mixture is poured into 250 ml of a saturated aqueous $NaHSO_4$ solution and 250 ml of water, the MeOH is dissolved in vacuo, and the solid is filtered off with suction. Drying in vacuo results in 2.0 g of colorless crystals, mp 138° C.

R$_f$ (DIP)=0.15 MS (DCI):321 (M)$^+$ f) Methyl 2-methyl-4-isopropyl-5-methylsulfonylaminobenzoate 28 ml of a 2M solution of isopropylmagnesium chloride in THF are added dropwise to 134 ml of a 0.5M solution of ZnCl$_2$ in THF, and the mixture is stirred at 55°–60° C. for 6 h. Then, at RT, 2.0 g of methyl 2-methyl-4-bromo-5-methylsulfonylaminobenzoate, 230 mg of CuI and 522 mg of [1,1'-bis-(diphenylphosphino)ferrocene] palladium(II) chloride are added, and the mixture is stirred at RT for 18 h. The reaction mixture is diluted with 500 ml of EA, and the precipitate is filtered off. After washing twice with 200 ml of 5% aqueous NaHSO$_4$ solution each time and twice with 200 ml of saturated aqueous NaCl solution each time and drying over Na$_2$SO$_4$ the solvents are removed in vacuo. Chromatography on silica gel with DIP affords 1.1 g of a colorless oil.

R$_f$ (DIP)=0.21 MS (DCI):286 (M+H)$^+$ g) 2-Methyl-4-isopropyl-5-methylsulfonylaminobenzoylguanidine 550 mg of methyl 2-methyl-4-isopropyl-5-methylsulfonylaminobenzoate are guanylated by the general method for the preparation of benzoylguanidines (I), Variant C (reaction time 3 h at 80° C.). 270 mg of an amorphous white powder are obtained.

R$_f$ (EA/MeOH 5:1)=0.41 MS (ES):313 (M+H)$^+$

Pharmacological data:

Inhibition of the Na$^+$/H$^+$ exchanger of rabbit erythrocytes White New Zealand rabbits (Ivanovas) received a standard diet containing 2% cholesterol for six weeks in order to activate Na$^+$/H$^+$ exchange and thus to make it possible to determine the Na$^+$ influx into the erythrocytes via Na$^+$/H$^+$ exchange by flame photometry. The blood was taken from the arteries of the ear and anticoagulated with 25 IU of potassium heparin. Part of each sample was used for duplicate determination of the hematocrit by centrifugation. Aliquots each of 100 μl were used to measure the Na$^+$ content of the erythrocytes.

In order to determine the amiloride-sensitive sodium influx, 100 μl of each blood sample were incubated in each case in 5 ml of a hyperosmolar salt/sucrose medium (mmol/l: 140 NaCl, 3 KCl, 150 sucrose, 0.1 ouabain, 20 trishydroxymethylaminomethane) at pH 7.4 and 37° C. The erythrocytes were then washed three times with ice-cold MgCl$_2$/ouabain solution (mmol/l: 112 MgCl$_2$, 0.1 ouabain) and hemolyzed in 2.0 ml of distilled water. The intracellular sodium content was determined by flame photometry.

The net Na$^+$ influx was calculated from the difference between the initial sodium levels and the sodium content of the erythrocytes after incubation. The sodium influx which could be inhibited by amiloride was found from the difference in the sodium content of the erythrocytes after incubation with and without amiloride 3×10$^{-4}$ mol/l. The same procedure was applied to the compounds according to the invention.

Results

Inhibition of the Na$^+$/H$^+$ exchanger:

| Example | IC$_{50}$ [μmol/l] |
|---------|---------------------|
| 1       | 0.3                 |
| 2       | 0.74                |

What is claimed is:

1. A benzoylguanidine of the formula I

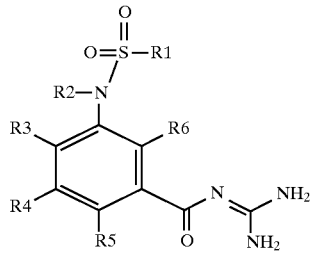

in which:

R(1) is an alkyl radical having 1, 2, 3, 4, 5, 6, 7 or 8 carbon atoms;

R(2) is hydrogen or an alkyl radical having 1, 2, 3, 4, 5, 6, 7 or 8 carbon atoms;

R(3) is hydrogen, —SR(25), —OR(25), —NR(25)R(26) or —CR(25)R(26)R(27);

R(25) is hydrogen, an alkyl radical having 1, 2, 3, 4, 5, 6, 7 or 8 carbon atoms or phenyl, which is unsubstituted or substituted by 1–3 substituents selected from the group consisting of F, Cl, CF$_3$, CH$_3$, methoxy, hydroxyl, amino, methylamino and dimethylamino;

or

R(25) is a pyridyl or pyrrolyl radical, which is unsubstituted or substituted by 1–3 substituents selected from the group consisting of the group F, Cl, CF$_3$, CH$_3$, methoxy, hydroxyl, amino, methylamino and dimethylamino;

R(26) and R(27) are, independently of one another, defined as R(25) or are hydrogen or an alkyl radical having 1, 2, 3, 4, 5, 6, 7 or 8 carbon atoms;

R(4) is hydrogen, F, Cl, Br, I, OH, —C≡N, CF$_3$, an alkyl radical having 1, 2, 3, 4, 5, 6, 7 or 8 carbon atoms, or an alkenyl radical having 2, 3, 4, 5, 6, 7 or 8 carbon atoms;

R(5) and R(6) are, independently of one another, hydrogen, an alkyl radical having 1, 2, 3 or 4 carbon atoms, F, Cl, —OR(32), —NR(33)R(34) or CF$_3$;

R(32), R(33) and R(34) are, independently of one another, hydrogen or alkyl having 1, 2, 3 or 4 carbon atoms;

or a pharmaceutically acceptable salt thereof.

2. A compound of the formula I as claimed in claim 1, in which: R(1) is an alkyl radical having 1, 2, 3, or 4 carbon atoms;

R(2) is hydrogen or an alkyl radical having 1, 2, 3, or 4 carbon atoms;

R(3) is hydrogen, —SR(25), —OR(25), —NR(25)R(26) or —CR(25)R(26)R(27);

R(25) is hydrogen, an alkyl radical having 1, 2, 3, or 4 carbon atoms or phenyl, which is unsubstituted or substituted by 1–2 substituents selected from the group consisting of F, Cl, CF$_3$, CH$_3$, methoxy, hydroxyl, amino, methylamino and dimethylamino;

or

R(25) is a pyridyl or pyrrolyl radical, which is unsubstituted or substituted by 1–2 substituents selected from the group consisting of the group F, Cl, CF$_3$, CH$_3$, methoxy, and dimethylamino;

R(26) and R(27) are, independently of one another, hydrogen or alkyl having 1, 2, 3 or 4 carbon atoms;

R(4) is hydrogen, F, Cl, Br, I, OH, CF$_3$, an alkyl radical having 1, 2, 3, or 4 carbon atoms, or an alkenyl radical having 2, 3, or 4 carbon atoms;

13

R(5) and R(6) are, independently of one another, hydrogen, an alkyl radical having 1, 2, or 3 carbon atoms, F, Cl, —OR(32), —NR(33)R(34) or $CF_3$;

R(32), R(33) and R(34) are, independently of one another, hydrogen or methyl;

or a pharmaceutically acceptable salt thereof.

3. A compound of the formula I as claimed in claim 1, in which:

R(1) is methyl;

R(2) is hydrogen, or methyl;

R(3) is hydrogen, —SR(25), —OR(25), —NR(25)R(26) or —CR(25)R(26)R(27);

R(25) is hydrogen, an alkyl radical having 1, 2, or 3 carbon atoms or phenyl, which is unsubstituted or substituted by one substituent selected from the group consisting of F, Cl, $CF_3$, and $CH_3$;

or

R(25) is a pyridyl or pyrrolyl radical, which is unsubstituted or substituted by one substituent selected from the group consisting of F, Cl, $CF_3$, and $CH_3$;

R(26) and R(27) are, independently of one another, hydrogen or methyl;

R(4) is hydrogen, F, Cl, OH, $CF_3$, an alkyl radical having 1, 2, 3, or 4 carbon atoms;

R(5) and R(6) are, independently of one another, hydrogen, an alkyl radical having 1, 2, or 3 carbon atoms, F, Cl, —OR(32), —NR(33)R(34) or $CF_3$;

R(32), R(33) and R(34) are, independently of one another, hydrogen or methyl;

or a pharmaceutically acceptable salt thereof.

4. A compound of the formula I as claimed in claim 1, in which:

R(1) is methyl

R(2) is hydrogen;

R(3) is hydrogen, —OR(25), or —CR(25)R(26)R(27);

R(25) is hydrogen, an alkyl radical having 1, 2, or 3 carbon atoms or phenyl, which is unsubstituted or substituted by one substituent selected from F, Cl, $CF_3$, and $CH_3$;

or

R(25) is a pyridyl or pyrrolyl radical, which is unsubstituted or substituted by one substituent selected from the group consisting of F, Cl, $CF_3$, and $CH_3$;

R(26) and R(27) are, independently of one another, hydrogen or methyl;

R(4) is hydrogen, OH, $CF_3$, an alkyl radical having 1, 2, 3, or 4 carbon atoms;

R(5) and R(6) are, independently of one another, hydrogen, an alkyl radical having 1, 2, or 3 carbon atoms, F, Cl or $CF_3$;

or a pharmaceutically acceptable salt thereof.

5. A compound I as claimed in claim 1, selected from the group comprising 4-isopropyl-3-methylsulfonylaminobenzoylguanidine, hydrochloride; 3-methylsulfonylamino-4-(3-pyridyloxy)benzoylguanidine;

14 and 2-methyl-4-isopropyl-5-methylsulfonylaminobenzoylguanidine.

6. A pharmaceutical composition comprising an effective amount for use as a pharmaceutical of a compound of the formula I as claimed in claim 1 together with a pharmaceutically acceptable carrier.

7. A method for the treatment of arrhythmias which comprises administering to a mammal in need of such treatment a pharmaceutical composition as set forth in claim 6.

8. A method for the treatment of arrhythmias which comprises administering to a mammal in need of such treatment an effective amount of a compound I as set forth in claim 1.

9. A method for the treatment or prophylaxis of myocardial infarcts which comprises administering to a mammal in need of such treatment or prophylaxis a pharmaceutical composition as set forth in claim 6.

10. A method for the treatment or prophylaxis of myocardial infarcts which comprises administering to a mammal in need of such treatment or prophylaxis an effective amount of a compound I as set forth in claim 1.

11. A method for the treatment or prophylaxis of angina pectoris which comprises administering to a mammal in need of such treatment or prophylaxis a pharmaceutical composition as set forth in claim 6.

12. A method for the treatment or prophylaxis of angina pectoris which comprises administering to a mammal in need of such treatment or prophylaxis an effective amount of a compound I as set forth in claim 1.

13. A method for the treatment or prophylaxis of ischemic states of the heart which comprises administering to a mammal in need of such treatment or prophylaxis a pharmaceutical composition as set forth in claim 6.

14. A method for the treatment or prophylaxis of ischemic states of the heart which comprises administering to a mammal in need of such treatment or prophylaxis an effective amount of a compound I as set forth in claim 1.

15. A method for the treatment or prophylaxis of ischemic states of the peripheral and central nervous system and of stroke which comprises administering to a mammal in need of such treatment or prophylaxis a pharmaceutical composition as set forth in claim 6.

16. A method for the treatment or prophylaxis of ischemic states of the peripheral and central nervous system and of stroke which comprises administering to a mammal in need of such treatment or prophylaxis an effective amount of a compound I as set forth in claim 1.

17. A method for the treatment of states of shock which comprises administering to a mammal in need of such treatment a pharmaceutical composition as set forth in claim 6.

18. A method for the treatment of states of shock which comprises administering to a mammal in need of such treatment an effective amount of a compound I as set forth in claim 1.

* * * * *